United States Patent
Saenger et al.

(10) Patent No.: US 6,468,280 B1
(45) Date of Patent: Oct. 22, 2002

(54) UNICOMPARTMENTAL REPLACEMENT INSTRUMENT AND METHOD

(75) Inventors: Paul L. Saenger, Asheville, NC (US); Richard J. Kana, Lexington, TX (US); Charles H. Perrone, Jr., Austin, TX (US)

(73) Assignee: Sulzer Orthopedics Inc., Austin, TX (US)

( * ) Notice: Subject to any disclaimer, the term of this patent is extended or adjusted under 35 U.S.C. 154(b) by 236 days.

(21) Appl. No.: 09/624,265

(22) Filed: Jul. 24, 2000

(51) Int. Cl.[7] ............................................. A61B 17/58
(52) U.S. Cl. ............................. 606/88; 606/87; 606/102
(58) Field of Search ............................. 606/86–88, 96, 606/102

(56) References Cited

U.S. PATENT DOCUMENTS

| | | | | |
|---|---|---|---|---|
| 5,122,144 A | * | 6/1992 | Bert et al. ..................... | 606/88 |
| 5,569,261 A | * | 10/1996 | Marik et al. ................... | 606/88 |
| 5,611,802 A | * | 3/1997 | Samuelson et al. ........... | 606/86 |
| 5,649,928 A | * | 7/1997 | Grundei ....................... | 606/88 |
| 5,662,656 A | * | 9/1997 | White .......................... | 606/88 |
| 5,676,668 A | * | 10/1997 | McCue et al. ................. | 606/87 |
| 5,688,281 A | * | 11/1997 | Cripe et al. ................... | 606/88 |
| 5,709,689 A | * | 1/1998 | Ferrante et al. ............... | 606/86 |
| 5,720,752 A | * | 2/1998 | Elliot et al. ................... | 606/88 |
| 5,810,831 A | * | 9/1998 | D'Antonio .................... | 606/88 |
| 5,916,219 A | * | 6/1999 | Matsuno et al. ............... | 606/88 |
| 5,980,526 A | * | 11/1999 | Johnson et al. ................ | 606/86 |
| 6,024,746 A | * | 2/2000 | Katz ............................ | 606/88 |
| 6,090,114 A | * | 7/2000 | Matsuno et al. ............... | 606/88 |
| 6,173,200 B1 | * | 1/2001 | Cooke et al. ................. | 600/425 |
| 6,258,095 B1 | * | 7/2001 | Lombardo et al. ............. | 606/88 |

OTHER PUBLICATIONS

Surgical Technique Brochure: "The Intermedics Natural–Knee Unicompartmental Replacement" Intramedics Orthopedics, Inc, Austin, Texas, © 1994.
Surgical Technique Brochure: "Natural–Knee Unicompartmental Replacement System" Catalog # 1000–02–669, 1990 Intramedics Orthopedics, Inc.

* cited by examiner

*Primary Examiner*—Ralph A. Lewis
(74) *Attorney, Agent, or Firm*—Philip Lyren

(57) ABSTRACT

A surgical instrument for establishing and verifying cutting depth and alignment includes a distal saw drill guide, a rod adaptor removably mounted on the distal saw drill guide and a modular alignment rod removably mounted on the rod adaptor. The distal saw drill guide includes pin apertures for receiving a plurality of pins for locating the distal saw drill guide on the distal end of a femur. A distal saw block is mounted on the pins in replacement of the distal saw drill guide the rod adaptor and the alignment rod. A stylus is adjustably attached to a stylus block which is movably mounted on the distal saw block. The rod adaptor and modular alignment rod are movably mounted on the distal saw block in replacement of the stylus and stylus block.

20 Claims, 4 Drawing Sheets

UNICOMPARTMENTAL REPLACEMENT INSTRUMENT AND METHOD

BACKGROUND

The disclosures herein relate generally to surgical instruments and more particularly to an instrument providing for a less invasive unicompartmental replacement procedure.

Unicompartmental knee replacement procedures ordinarily require a relatively large incision. The patella is usually displaced and inverted to obtain adequate exposure of the joint and the required anatomical references for proper alignment of cutting blocks and/or guides.

Routinely a rod, referred to as an intramedullary rod, is inserted into the femoral intramedullary canal from the distal end of the femur. This rod is used for alignment purposes for cutting block and/or guides.

This familiar method is considered an acceptable technique but is also know to cause trauma to the tissues involved. When a lesser amount of trauma is caused by a surgical procedure, less time is needed for patient recovery.

Most surgical techniques for a unicompartmental replacement procedure include a relatively large incision with displacement and/or inversion of the patella. This adequately exposes for femur for use of instrumentation to determine proper alignment and depth of bone resection.

A hole is typically drilled through the distal portion of the femur and into the intramedullary canal. This hole is relatively large and is required for the insertion of an intramedullary rod. The rod aligns itself with the inner canal of the femur, and then using other instruments which reference the intramedullary rod, the surgeon determines alignment of the joint.

One current system offers an extramedullary technique whereby the entire length of the canal is not violated. However, this technique is not entirely or truly extramedullary. A hole must still be drilled into the distal portion of the femur and a short portion of the canal is still violated. This drilling will normally require patella displacement.

Alignment is required for positioning of saw blocks and/or saw guides which are used during resection of the distal femur bone. This is a commonalty with all systems. During typical procedures, when the intramedullary rod is inserted into the intramedullary canal, a compressing of the natural materials and fluids inside the canal occurs. This can have undesirable consequences in some patients. Therefore, avoiding violation of the intramedullary canal during such a procedure is preferable.

Therefore, what is needed is an instrument and a method to lessen the morbidity of the exposure by precluding the need to displace and/or invert the patella, and to avoid violating the intramedullary canal while still allowing proper alignment of instrumentation for bone resection.

SUMMARY

One embodiment, accordingly, provides a less invasive unicompartmental replacement surgical instrument and method for establishing and verifying cutting depth and alignment. To this end, the surgical instrument includes a distal saw drill guide, a rod adapter removably mounted on the distal saw drill guide and a modular alignment rod removably mounted on the rod adaptor.

Cutting depth may be verified by replacing the distal saw drill guide with a distal saw block and a stylus. Alignment may be verified by attaching the rod adaptor and the modular alignment rod to the distal saw block.

A principal advantage of this embodiment is that it provides for a less invasive unincompartmental replacement procedure which reduces the morbidity of exposure by avoiding the need to displace the patella, and also avoids violating the intramedullary canal.

BRIEF DESCRIPTION OF THE DRAWING FIGURES

DETAILED DESCRIPTION

Figure 1:
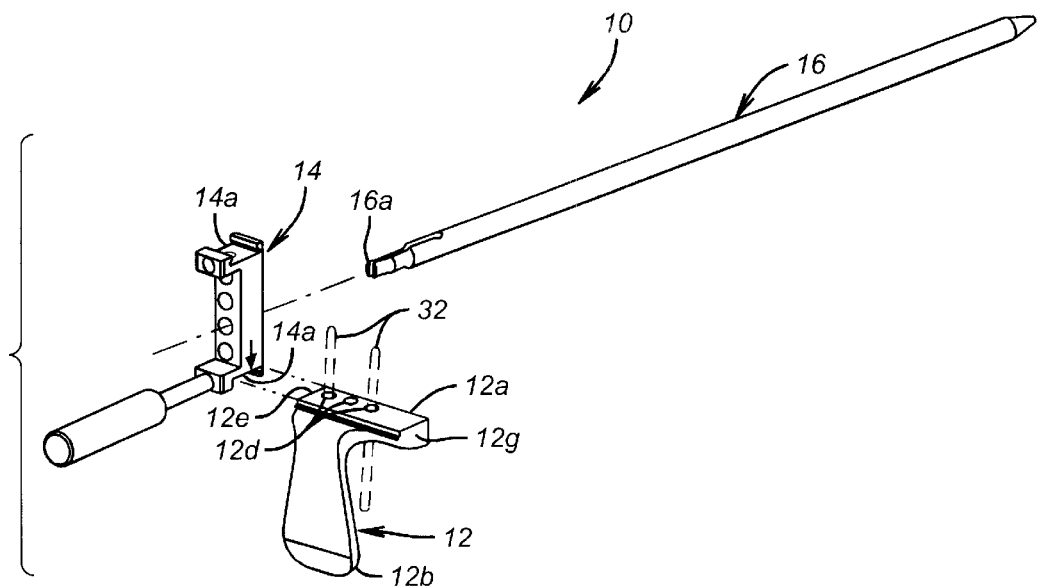
FIG. 1 is an exploded perspective view illustrating an embodiment of a surgical instrument for a unicompartmental replacement.

A surgical instrument for establishing cutting depth and alignment includes an assembly 10, FIG. 1, having a distal saw drill guide 12, a rod adaptor 14 removably mountable on the distal saw drill guide 12 and modular alignment rod 16, removably mountable on the rod adaptor 14.

Figure 2:
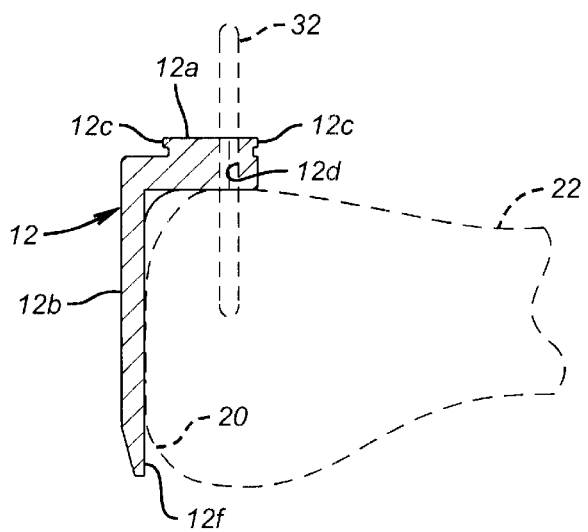
FIG. 2 is a cross-sectional side view illustrating an embodiment of a distal saw drill guide.

The distal saw drill guide 12, FIGS. 1 and 2, is generally "L" shaped and includes a receiver portion 12a and a reference portion 12b substantially at a right angular relationship with receiver portion 12a. Receiver portion 12a may include pair opposed guides 12c for receiving the rod adaptor 14, discussed below. Receiver portion 12a also includes a plurality of pin apertures 12d, formed therethrough. The pin apertures 12d permit pin holes to be located and drilled in a femur 22 so that a plurality of pins 32 can be driven therein to locate the guide 12 and establish a cutting depth for resecting a distal end 20 of the femur 22.

The reference portion 12b is an elongated extension offset to a side 12e relative to receiver portion 12a, including a substantially planar surface 12f for resting against the distal end 20 of the femur 22. Two of the distal saw drill guides 12 may be provided. One is offset to the side 12e for use in a right medial, left lateral procedure. The other (not shown) is offset to a side 12g for a left medial, right lateral procedure.

Figure 3A:
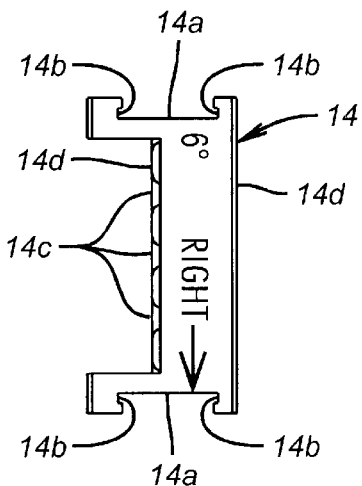
FIGS. 3A and 3B are right and left side views, respectively, illustrating an embodiment of a rod adaptor.
Figure 3B:
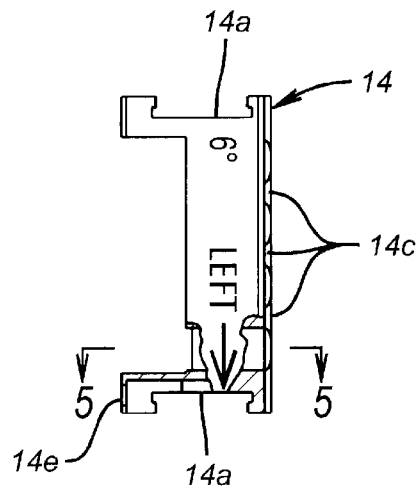
Figure 5:
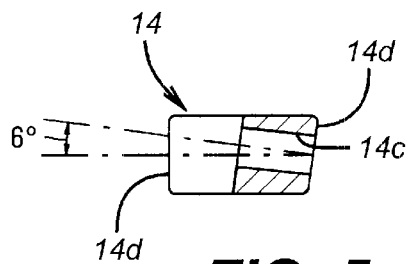
FIG. 5 is a view taken along the line 5—5 of FIG. 3B.
Figure 4:
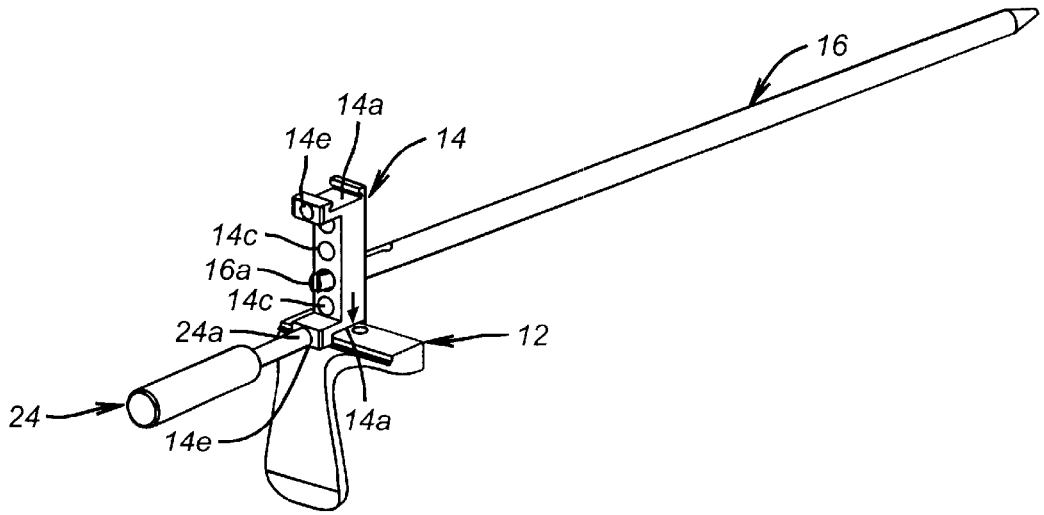
FIG. 4 is an assembled view of the instrument of FIG. 1.

The rod adaptor 14, FIGS. 3A, 3B and 4, is generally in the shape of a block having a pair of opposed grooves 14a at opposite ends thereof. The grooves 14a may include a dove-tail or slotted portion 14b for engagement with guides 12c so that the rod adaptor 14 may be movably mounted on the distal saw drill guide 12. The opposed grooves 14a permit use of the adaptor 14 for either a right or a left knee surgery. A plurality of rod receiving apertures 14c are formed in rod adaptor 14 for receiving the alignment rod 16, discussed below. A pair of opposed faces 14d, along with the apertures 14c, are formed with a built-in 6 degree angle, FIG. 5, to provide for a standard anatomical alignment for establishing the alignment of rod 16 relative to the femur 22. A pair of threaded apertures 14e, FIGS. 3B and 4, are each formed adjacent a respective pair of the grooves 14a. In this manner, an adjustable member such as a handle 24, including a threaded end 24a, can be received in one of the apertures 14e and advanced to engage the distal saw drill guide 12 so as to secure the adaptor 14 in a stationary position with respect to the distal saw drill guide 12. Alignment rod 16 includes a split end 16a which is flexible for snap-in engagement with the rod receiving apertures 14c in rod adaptor 14.

Figure 6:
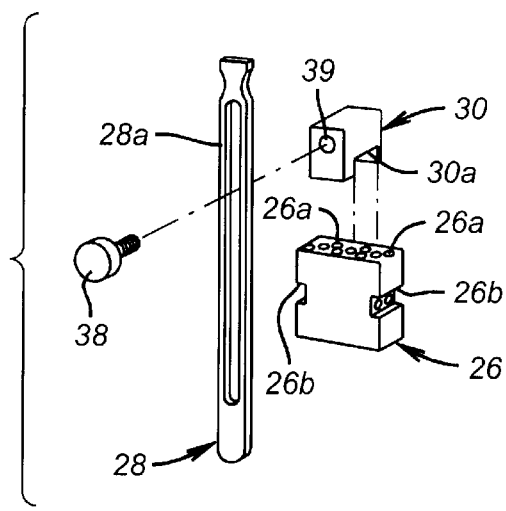
FIG. 6 is an exploded perspective view illustrating an embodiment of a stylus, a stylus block and a distal saw block.

A distal saw block 26, FIG. 6, is generally rectangular and includes a plurality of pin apertures 26a formed therethrough. The pin apertures 26a permit the saw block 26 to be mounted on the pins 32, discussed above. Pin apertures 26a are provided in rows, each row having a separation from each other row by about 2 mm distance. This separation provides for adjusting the depth of a cut to resect bone at the distal end 20 of femur 22, discussed above.

Figure 7:
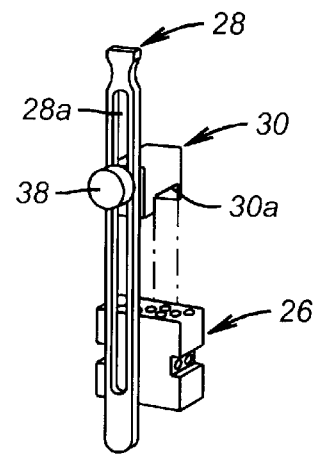
FIG. 7 is another view of the stylus, stylus block and distal saw block.
Figure 8:
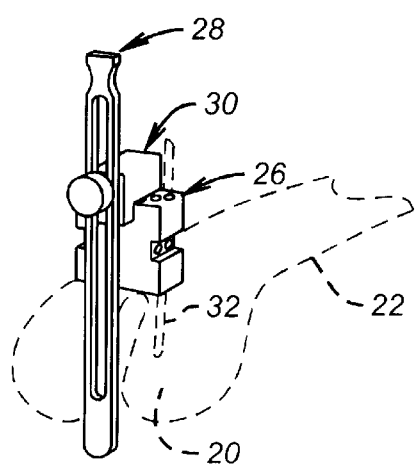
FIG. 8 is a further view of the stylus, stylus block and distal saw block.

A sylus 28 and a stylus block 30, FIG. 7, can be mounted on the saw block 26. Stylus 28 is an elongated member including an elongated slot 28a formed therein. Stylus block 30 is generally rectangular and includes a groove 30a formed therein for movably seating stylus block 30 on distal saw block 26. A threaded adjustment member 38, FIG. 6, extends through slot 28a and into a threaded receiver 39 in stylus block 30. In this manner, stylus 28 can be positioned relative to stylus block 30 by advancing the adjustment member 38 and securing the stylus 28 on stylus block 30. In so doing, when the stylus block 30 is seated on distal saw block 26, FIG. 8, stylus 28 can be extended adjacent the distal end 20 of femur 22 to verify the depth of the cut based on the pinned location of the distal saw block 26.

Figure 9:
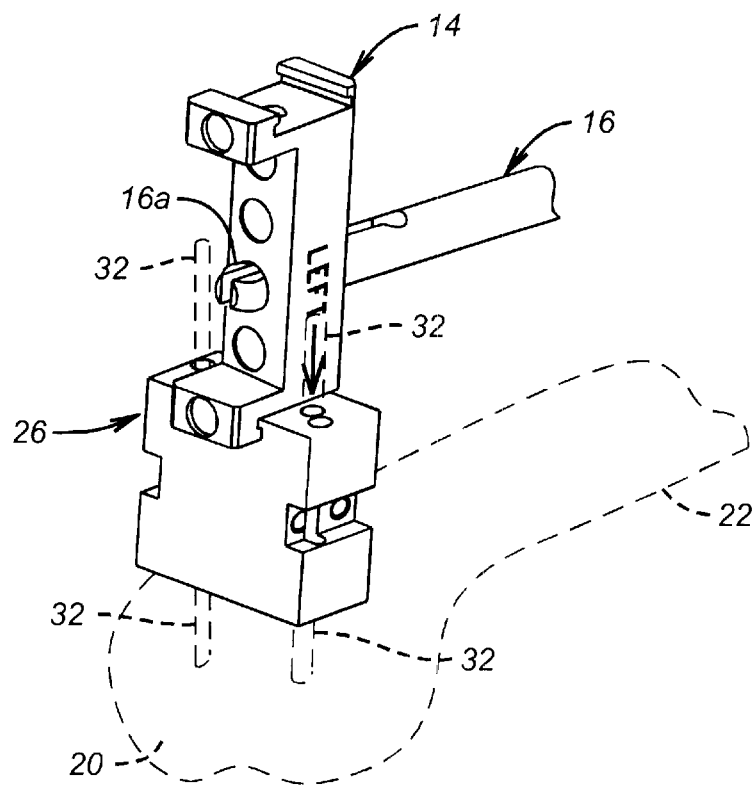
FIG. 9 is a perspective view illustrating an embodiment of the rod adaptor, alignment rod and distal saw block.

Upon satisfactory verification of the cutting depth, the stylus 28 and stylus block 30 are removed from distal saw block 26, FIG. 9. Thereafter, the rod adaptor 14 and rod 16 may be movably seated on the distal saw block 26 so that alignment of the rod 16 relative to the femur 22 can be verified.

Figure 10:
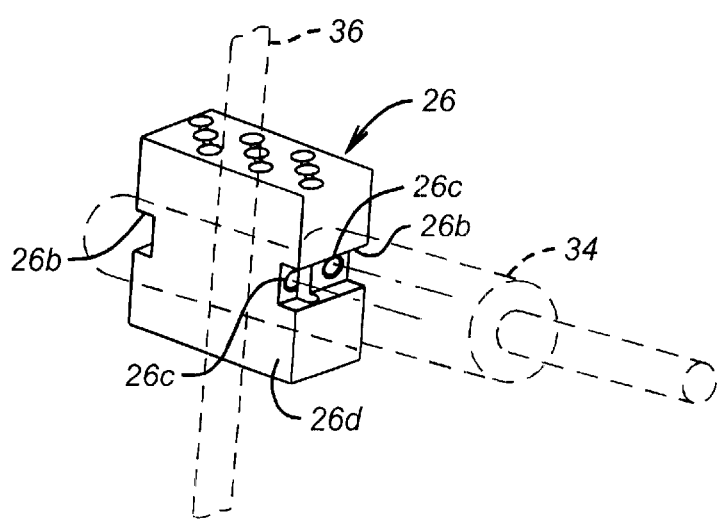
FIG. 10 is a perspective view illustrating an embodiment of the distal saw block, a saw guide and a saw blade.

A pair of opposed grooves 26b, FIG. 10, are interconnected by a pair of spaced apart apertures 26c for receiving a saw guide 34 illustrated in phantom. The saw guide 34 can be used to enhance the quality and reliability of a cut by guiding a saw blade 36, along a planar surface 26d of distal saw block 26.

In operation, the distal saw drill guide 12 is positioned on the distal end 20 of the femur 22. The rod adaptor 14 is removably mounted on the distal saw drill guide 12. The alignment rod 16 is removably mounted in the rod adaptor 14 so that the rod 16 extends for establishing an alignment with the femur 22. The handle 24 may be used for maintaining the rod adaptor 14 positioned on the distal saw drill guide 12. Using the pin apertures 12d as guides, holes are drilled in the distal end 20 of the femur 22. Pins 32 are driven through the pin apertures 12d and into the drilled holes for locating the distal saw drill guide 12. In this manner, a cutting depth is established for resecting the distal end 20 of the femur 22.

The distal saw drill guide 12, the rod adaptor 14 and the alignment rod 16 are removed from the pins and the distal saw block 26 is mounted on the pins 32 in replacement of the distal saw drill guide 12, the rod adaptor 14 and the rod 16. The stylus 28 and stylus block 30 are mounted on the distal saw block 26 and may be adjusted for verifying the cutting depth. The stylus 28 and stylus block 30 are removed from the distal saw block 26 and replaced by the rod adaptor 14 and the alignment rod 16 for verifying the alignment of the alignment rod 16 with the femur 22. A saw guide 34 may be attached to the distal saw block 26 for guiding the saw blade 36 when the distal end 20 of the femur 22 is being cut.

As a result, one embodiment provides a surgical instrument for establishing cutting depth and alignment including a distal saw drill guide, a rod adaptor removably mounted on the distal saw drill guide and a modular alignment rod removably mounted on the rod adaptor.

Another embodiment provides a unicompartmental replacement surgical instrument including a distal saw drill guide, a rod adaptor removably mounted on the distal saw drill guide and a modular alignment rod removably mounted on the rod adaptor. The distal saw drill guide includes pin apertures for receiving a plurality of pins for locating the distal saw drill guide. A distal saw block is mounted on the pins in replacement of the distal saw drill guide, the rod adaptor and the modular alignment rod. A stylus is adjustably mounted on the distal saw block and the rod adaptor and modular alignment rod are movably mounted on the distal saw block in replacement of the stylus.

Still another embodiment provides a surgical instrument for establishing and verifying cutting depth and alignment including a distal saw drill guide, a rod adaptor removably mounted on the distal saw drill guide and a modular alignment rod removably mounted on the rod adaptor. The distal saw drill guide includes pin apertures for receiving a plurality of pins for locating the distal saw drill guide and establishing cutting depth and alignment. A distal saw block is mounted on the pins in replacement of the distal saw drill guide, the rod adaptor and the modular alignment rod. A stylus is adjustably attached to a stylus block which is movably mounted on the distal saw block for verifying cutting depth. The rod adaptor and modular alignment rod are movably mounted on the distal saw block in replacement of the stylus and stylus block for verifying alignment.

A further embodiment provides a method of establishing and verifying cutting depth and alignment for bone resection. A distal saw drill guide is positioned on an end of a skeletal member. A rod adaptor is removably mounted on the distal saw drill guide. An alignment rod is removably mounted on the rod adaptor so that the rod extends for establishing an alignment with the skeletal member. The distal saw drill guide is located on the end of the skeletal member by a plurality of pins for establishing a cutting depth of the end of the skeletal member. The distal saw drill guide, the rod adaptor and the alignment rod are removed. A distal saw block is mounted on the pins in replacement of the distal saw drill guide, the rod adaptor and the alignment rod. A stylus is adjustably mounted on the distal saw block for verifying the cutting depth. The stylus is removed from the distal saw block and the rod adaptor and alignment rod are movably mounted on the distal saw block in replacement of the stylus for verifying the alignment of the alignment rod with the skeletal member.

As it can be seen, the principal advantages of these embodiments are that the instrument allows for a smaller incision to be made. Inversion of the patella is not required and displacement of the patella is kept to a minimum. It is not necessary to drill a comparatively large hole into the distal portion of the femur as is required in present known procedures. Also, it is not necessary to force an intramedullary rod into the femoral canal. Trauma to muscles and surrounding tissue is reduced. In addition, recovery time is shortened, therefore reducing potential pain and discomfort during recovery.

Although illustrative embodiments have been shown and described, a wide range of modification change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A surgical instrument for establishing cutting depth and alignment in a femur, comprising:
   a distal saw drill guide having a receiver portion with at least one aperture adapted to receive a drill and having a reference portion with a planar surface adapted to rest against a distal end of the femur, wherein the reference portion is at substantially a right angle to the receiver portion;
   a rod adapter having at least one groove to slideably engage the receiver portion and having at least one aperture; and
   a modular alignment rod removably mounted to the aperture of the rod adapter.

2. The instrument as defined in claim 1 wherein the distal saw drill guide has an "L" shape.

3. The instrument as defined in claim 1 wherein the rod adapter has a block shape and is removable from the saw drill guide.

4. The instrument as defined in claim 3 wherein the rod adapter has a first groove along one side of the block; a second groove along another side of the block; and the first and second grooves being on opposite sides of the block.

5. The instrument as defined in claim 4 wherein the receiver portion of the saw drill guide includes a pair of guides adapted to receive and slideably engage the first and second grooves of the rod adapter.

6. The instrument as defined in claim 1 further comprising a handle that removably attaches to the rod adapter.

7. The instrument as defined in claim 1 wherein the alignment rod has an elongated cylindrical configuration; and the rod adapter has a plurality of apertures for receiving and engaging an end of the alignment rod.

8. The instrument as defined in claim 1 wherein the saw drill guide includes a plurality of apertures adapted to receive a pin for mounting the saw drill guide against the femur.

9. The instrument as defined in claim 1 wherein the reference portion is an elongated extension that is offset relative to the receiver portion.

10. A unicompartmental replacement surgical instrument comprising:
    a distal saw drill guide;
    a rod adaptor removably mounted on the distal saw drill guide;
    a modular alignment rod removably mounted on the rod adaptor;
    the distal saw drill guide including pin apertures therein for receiving a plurality of pins for locating the distal saw drill guide;
    a distal saw block for mounting on the pins in replacement of the distal saw drill guide, the rod adaptor and the modular alignment rod;
    a stylus adjustably mounted on the distal saw block; and
    the rod adaptor and modular alignment rod being movably mounted on the distal saw block in replacement of the stylus.

11. The instrument as defined in claim 10 further comprising an adjustable member removably mounted on the rod adaptor and adjustable for maintaining the rod adaptor positioned on the distal saw drill guide.

12. The instrument as defined in claim 11 wherein the adjustable member includes a handle.

13. The instrument as defined in claim 11 further comprising a stylus block adjustably attached to the stylus for interconnecting the stylus and the distal saw block.

14. A surgical instrument for establishing and verifying cutting depth and alignment comprising:
    a distal saw drill guide;
    a rod adaptor removably mounted on the distal saw drill guide;
    a modular alignment rod removably mounted on the rod adaptor;
    the distal saw drill guide including pin apertures therein for receiving a plurality of pins for locating the distal saw drill guide for establishing cutting depth and alignment;
    a distal saw block for mounting on the pins in replacement of the distal saw drill guide, the rod adaptor and the modular alignment rod;
    a stylus adjustably attached to a stylus block, the stylus block being movably mounted on the distal saw block for verifying cutting depth; and
    the rod adaptor and modular alignment rod being movably mounted on the distal saw block in replacement of the stylus and stylus block for verifying alignment.

15. The instrument as defined in claim 14 further comprising an adjustable member removably mounted on the rod adaptor and adjustable for maintaining the rod adaptor positioned on the distal saw drill guide.

16. The instrument is defined in claim 15 wherein the adjustable member includes a handle.

17. A method of establishing and verifying cutting depth and alignment for bone resection comprising the steps of:
    positioning a distal saw drill guide on an end of a skeletal member;
    removably mounting a rod adaptor on the distal saw drill guide;
    removably mounting an alignment rod on the rod adaptor so that the rod extends for establishing an alignment with the skeletal member;
    locating the distal saw drill guide on the end of the skeletal member by a plurality of pins for establishing a cutting depth of the end of the skeletal member;
    removing the distal saw drill guide, the rod adaptor and the alignment rod;
    mounting a distal saw block on the pins in replacement of the distal saw drill guide, the rod adaptor and the alignment rod;
    adjustably mounting a stylus on the distal saw block for verifying the cutting depth;
    removing the stylus from the distal saw block; and
    movably mounting the rod adaptor and the alignment rod on the distal saw block in replacement of the stylus for verifying the alignment of the alignment rod with the skeletal member.

18. The method as defined in claim 17 further comprising the step of removably mounting an adjustable member on the rod adaptor for maintaining the rod adaptor positioned on the distal saw drill guide.

19. The method as defined in claim 17 wherein the step of locating the distal saw drill guide includes the steps of inserting the pins through apertures in the distal saw drill guide and driving the pins into the skeletal member.

20. The method as defined in claim 17 further comprising the step of attaching a saw guide to the distal saw block.

* * * * *